United States Patent
Wu et al.

(10) Patent No.: US 6,742,383 B2
(45) Date of Patent: Jun. 1, 2004

(54) DILUTER TO REDUCE QUANTITY OF MICRO PARTICLES IN THE AIR SO AS TO FACILITATE CALCULATION OF CONCENTRATION OF THE MICRO PARTICLES IN THE AIR

(75) Inventors: His-Sheng Wu, Hsinchu Hsien (TW); Hsu-Cheng Chiang, Hsinchu Hsien (TW); Tsun-Huo Ho, Hsinchu (TW)

(73) Assignee: Industrial Technology Research Institute (TW)

( * ) Notice: Subject to any disclaimer, the term of this patent is extended or adjusted under 35 U.S.C. 154(b) by 0 days.

(21) Appl. No.: 10/288,156

(22) Filed: Nov. 5, 2002

(65) Prior Publication Data

US 2004/0083791 A1 May 6, 2004

(51) Int. Cl.$^7$ .............................. G01N 1/38; B01F 3/02; B01D 46/00
(52) U.S. Cl. .................... 73/28.01; 73/28.04; 55/350.1; 55/482
(58) Field of Search ............................ 73/28.01, 28.03, 73/28.04; 55/350.1, 482

(56) References Cited

U.S. PATENT DOCUMENTS 6,602,328 B2 * 8/2003 Doi et al. ...................... 95/278
2002/0166390 A1 * 11/2002 Graze, Jr. .................. 73/28.01
2003/0131654 A1 * 7/2003 Robertson et al. ......... 73/28.04

FOREIGN PATENT DOCUMENTS

| JP | 2001-38129 | * | 2/2001 | ................ 55/350.1 |
| SU | 1153963 | * | 5/1985 | ................ 73/28.04 |

* cited by examiner

*Primary Examiner*—Daniel S. Larkin
(74) *Attorney, Agent, or Firm*—Schwegman, Lundberg, Woessner & Kluth, P.A.

(57) ABSTRACT

A diluter includes a filtering assembly and an intake assembly. The filtering assembly has a top cap that is provided with a first connector and a first through hole defined through the top cap, a lower cap having a second connector, a second through hole defined through the lower cap and an assembly hole defined to communicate with the second through hole, and a tubular filter securely connected between the top cap and the lower cap to form a mixing zone in communication with the first and the second through holes. The intake assembly having a first end and a second end, the first end being defined with a receiving hole to correspond to the first connector and the second end being provided with an inlet to communicate the first end and the second end.

18 Claims, 6 Drawing Sheets

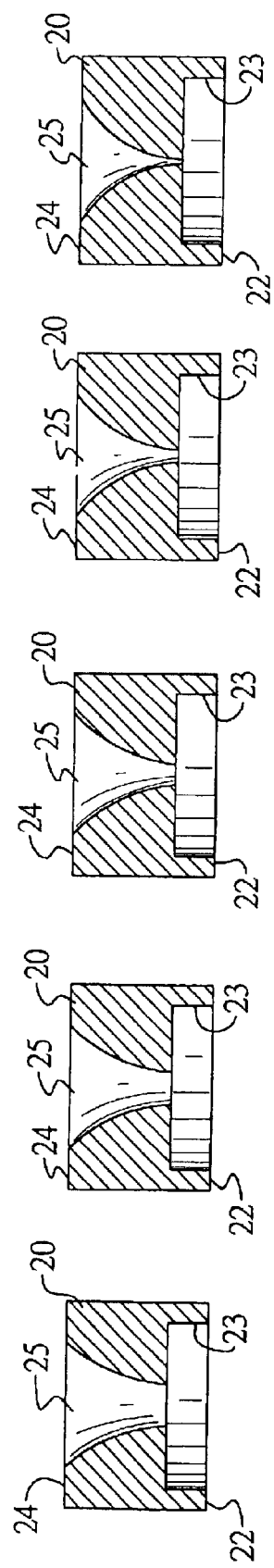

DILUTER TO REDUCE QUANTITY OF MICRO PARTICLES IN THE AIR SO AS TO FACILITATE CALCULATION OF CONCENTRATION OF THE MICRO PARTICLES IN THE AIR

BACKGROUND OF THE INVENTION

1. Field of the Invention

The present invention relates to a diluter, and more particularly to a diluter to reduce the quantity of micro particles in the air so as to facilitate calculation of the concentration of the micro particles in the air.

2. Description of Related Art

A conventional diluter mainly is adapted to be used with a particle counter so that particles in the air are able to be sampled by the diluter and then counted by the particle counter. Although the conventional diluter is able to take samples from the air directly, the size and the short life span of the diluter are the drawbacks in the field. The size of the diluter normally is big as a machine so that portability of the diluter is almost impossible. Furthermore, the conventional diluter has a fixed dilution ratio so that the user will have to prepare different diluters so as to cope with different sampling airs with various particle sizes.

To overcome the shortcomings, the present invention tends to provide an improved diluter to mitigate and obviate the aforementioned problems.

SUMMARY OF THE INVENTION

The primary objective of the present invention is to provide an improved diluter to reduce the quantity of micro particles in the air so as to facilitate calculation of concentration of the micro particles in the air.

In order to accomplish the foregoing objective, the diluter of the present invention has a filtering assembly and an intake assembly detachably connected to the filtering assembly. The filtering assembly has a top cap, a lower cap, and a high efficiency filter securely connected between the top cap and the lower cap. The intake assembly comprises a series of tubular heads each with a trumpet-like inlet that has a unique size so that each of the tubular heads is able to be selected to cope with micro particles of different sizes, which enables the diluter of the present invention to have the ability to take samples of airs with different concentrations of micro particles.

Other objects, advantages and novel features of the invention will become more apparent from the following detailed description when taken in conjunction with the accompanying drawings.

BRIEF DESCRIPTION OF THE DRAWINGS

FIGS. 6A to 6E are cross sectional views of the tubular heads of the intake assembly of the present invention.

DETAILED DESCRIPTION OF THE PREFERRED EMBODIMENT

Figure 1:
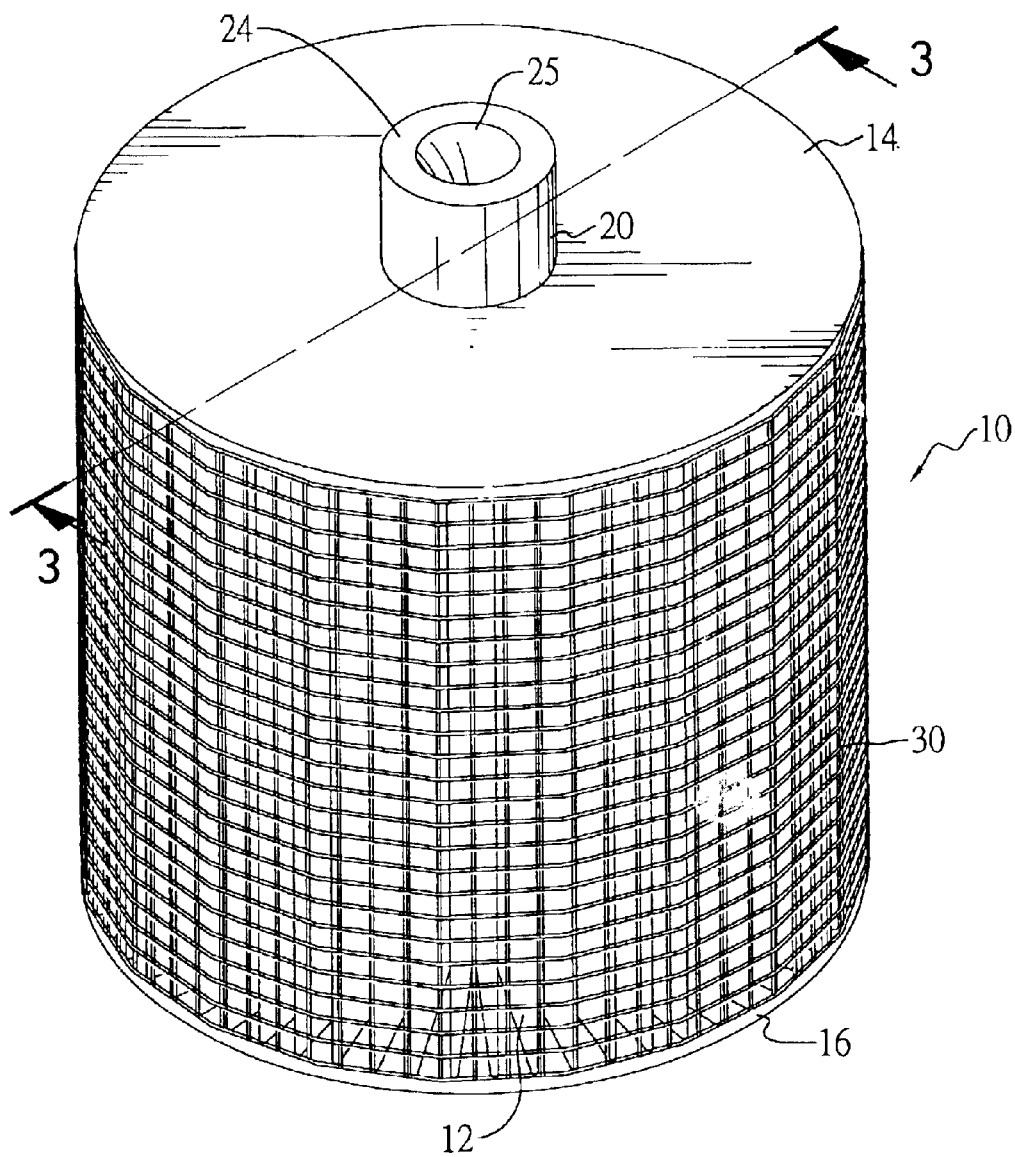
FIG. 1 is a perspective view of the diluter of the present invention.
Figure 2:
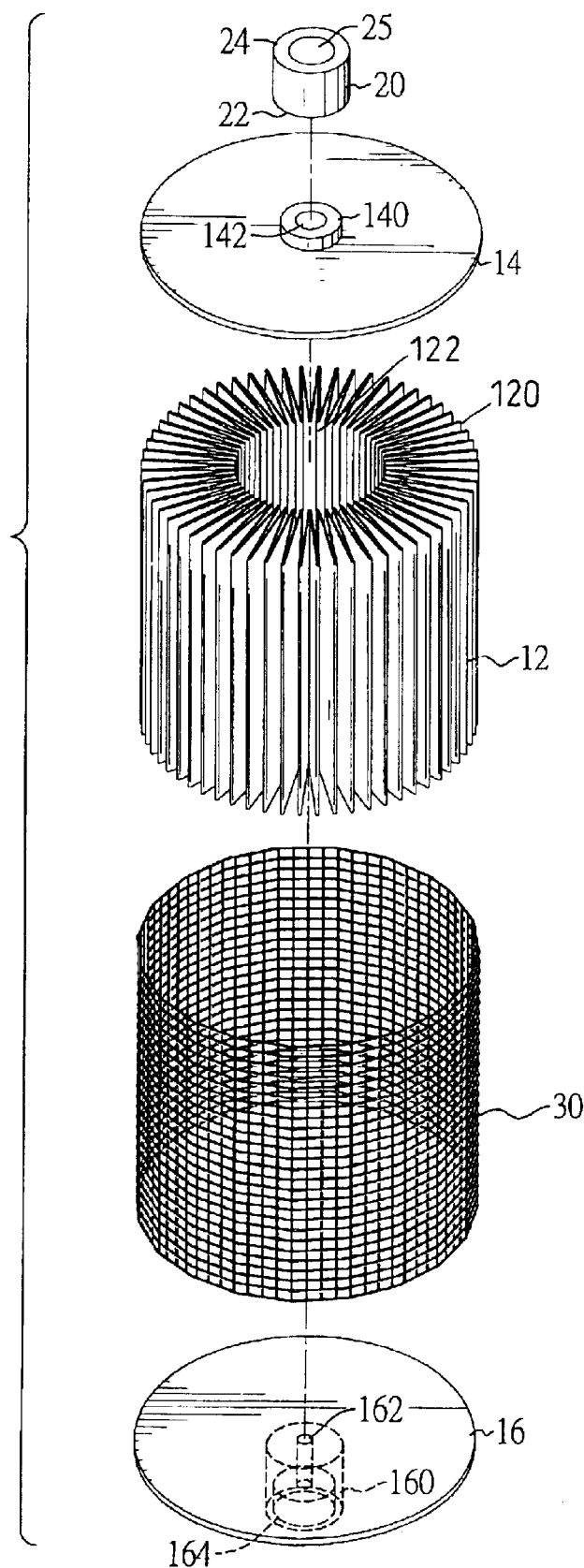
FIG. 2 is an exploded perspective view of the diluter in FIG. 1.

With reference to FIGS. 1 and 2, the diluter of the present invention has a filtering assembly (10), an intake assembly (20), and a tubular porous grill (30).

The filtering assembly (10) includes a top cap (14), a filter (12) and a lower cap (16). The top cap (14) has a first connector (140) securely formed on a top face of the top cap (14) and provided with a first through hole (142) extending through the top cap (14). The filter (12) is tubular and is made of a sheet of filtering material such as non-woven cloth and is folded to have multiple outer ridges (120) and inner ridges (122). The lower cap (16) has a second connector (160) securely formed on a bottom face of the lower cap (16) and having a second through hole (162) extending through the lower cap (16) to have a diameter smaller than that of the first through hole (142) and an assembly hole (164) defined in the bottom face of the lower cap (16) to communicate with the second through hole (162).

The intake assembly (20) of the present invention has a first end (22) and a second end (24). The first end (22) has a connecting hole (23) defined to receive therein the first connector (140) and the second end (24) has a trumpet-like inlet (25) in communication with the connecting hole (23), wherein the trumpet-like inlet (25) has a small diameter being less than a diameter of the second through hole (162).

The porous grill (30) is tubular with two open ends and is provided to surround an outer periphery of the filter (12) so that a user is able to hoid the diluter of the present invention.

Figure 3:
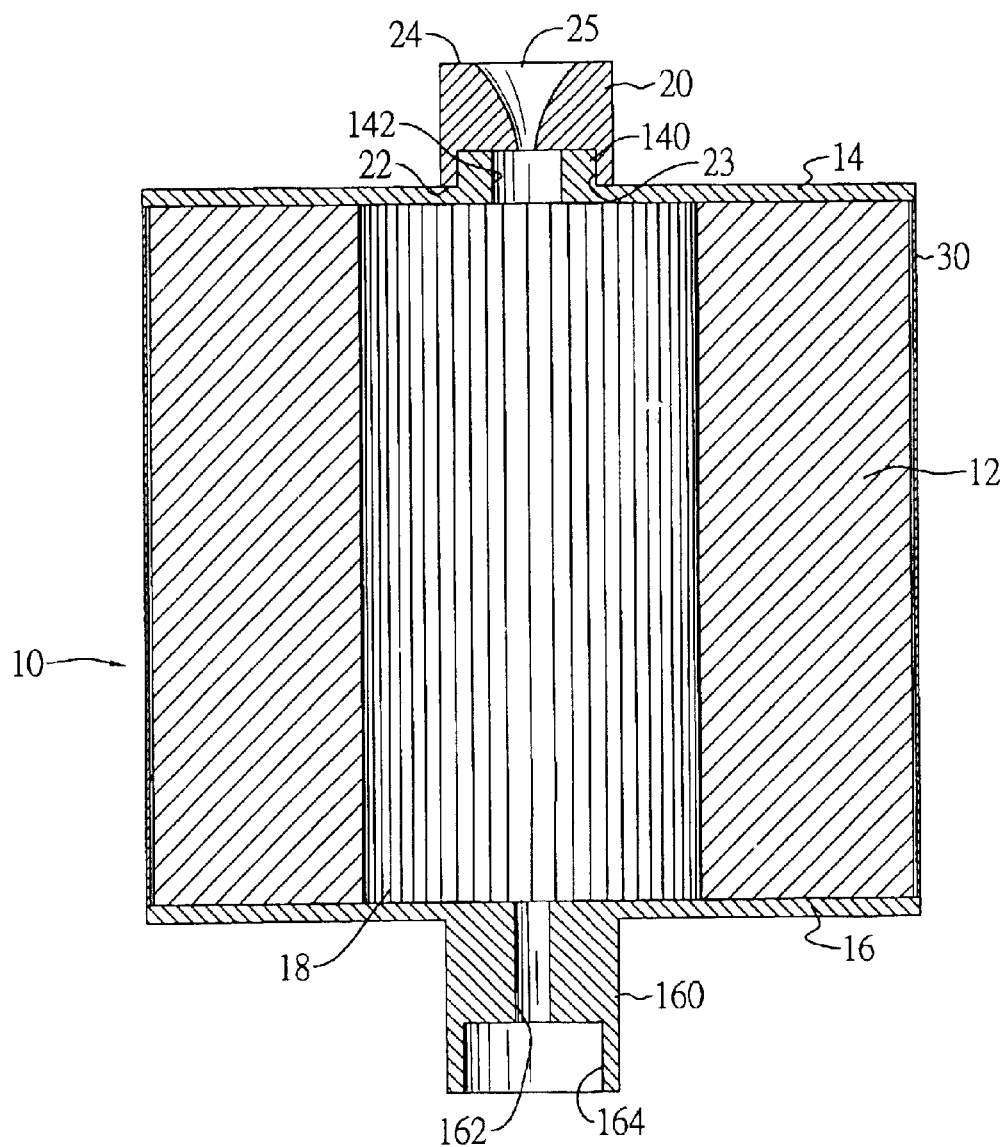
FIG. 3 is a cross sectional view of the diluter of the present invention in FIG. 1.

With reference to FIG. 3, when assembled, the intake assembly (20) is connected to the first connector (140) by receiving the first connector (140) in the connecting hole (23). The second connector (160) is connected to a particle counter (not shown) so that a mixing zone (18) is formed between the top cap (14) and the lower cap (16) and inside the filter (12).

When the particle counter is initiated, air is then sucked into the particle counter through the filter (12) and the inlet (25). Because the inlet (25) has a diameter different to that of apertures (not shown) in the filter (12), air passing through the inlet (25) and the filter (12) encounters different resistance. The relationship between the resistances can be calculated and expressed by a ratio. After the air passes through the inlet (25) and the filter (12), the air is mixed in the mixing zone (18) and then is sent to the particle counter, which accomplishes the purpose of diluting air.

Figure 4:
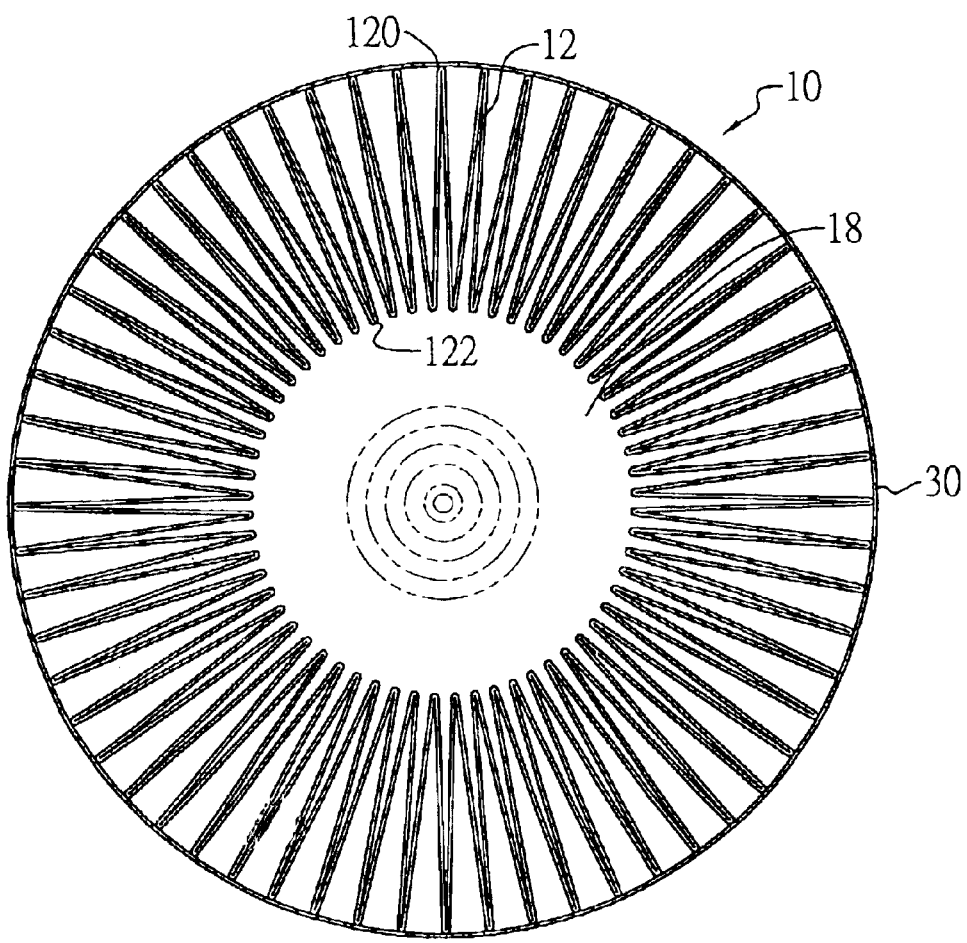
FIG. 4 is a top plan view of the filter used in the diluter of the present invention.

With reference to FIG. 4, because the filter (12) is formed by a sheet of non-woven cloth and is folded to have multiple outer ridges (120) and inner ridges (122), faces are formed between every two adjacent outer and inner ridges (120, 122). Therefore, filtering area is increased when compared to a conventional diluter. Meantime, the life span of the diluter is also increased due to the addition of the filter area.

Figure 5:
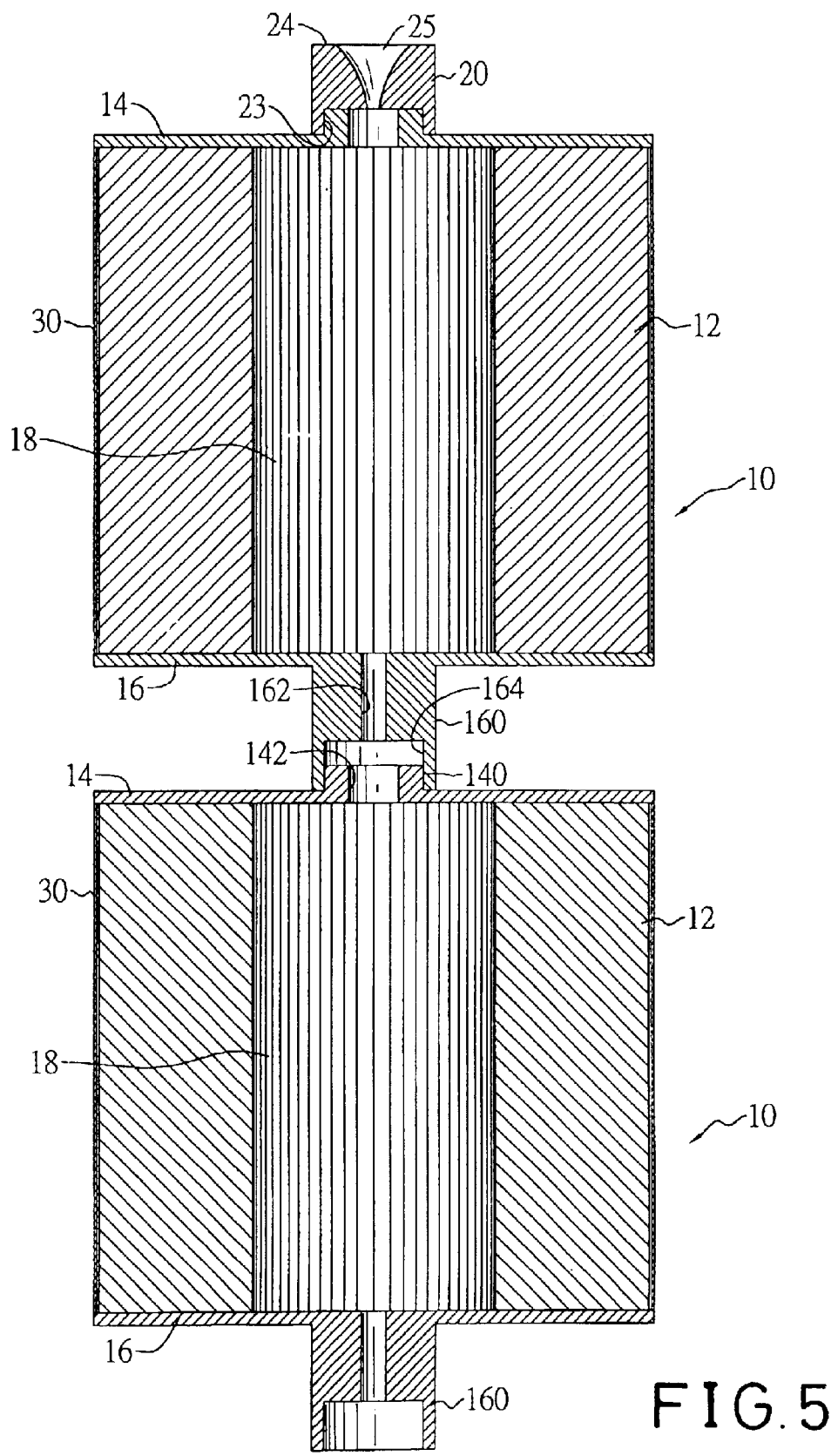
FIG. 5 is a cross sectional view of another embodiment of the present invention.

With reference to FIG. 5, when taking a sample in the air with a high density of particles is necessary, the user may combine two diluters by mating the first connector (140) of one diluter with the intake assembly (20) and the second connector (160) of the diluter with the first connector (140) of the other diluter. That is, the first connector (140) of one diluter is received in the connecting hole (23) of the intake assembly (20) and the first connector (140) of the other diluter is received in the assembly hole (164) of the diluter that is connected to the intake assembly (20).

After the combination of two diluters, the second connector (160) of the other diluter is then connected to the particle counter. With the combination of the diluters, the ability of air dilution is increased and the life span of the diluter is thus maintained. However, the number of combining the diluters is not limited, and the user is able to combine as many diluters as required.

With reference to FIGS. 6A to 6E, it is noted that the intake assembly (20) has a series of tubular heads each with a trumpet-like inlet (25). Each inlet (25) has a unique dimension so that the user is able to replace one tubular head for another tubular head. Thus, the ability to test air samples with different particle concentrations is increased.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A diluter comprising:
   a filtering assembly having
   a top cap that is provided with a first connector formed on a top face of the top cap and a first through hole defined through the top cap;
   a lower cap having a second connector securely formed on a bottom face of the lower cap, a second through hole defined through the lower cap and an assembly hole defined to communicate with the second through hole; and
   a tubular filter securely connected between the top cap and the lower cap to form a mixing zone in communication with the first and the second through holes; and
   an intake assembly having a first end and a second end, the first end being defined with a receiving hole to correspond to the first connector and the second end being provided with an inlet to communicate with the first end and the second end,
   whereby after the first connector is received in the receiving hole and the assembly hole of the second connector is adapted to connect to a particle counter, the particle counter is able to calculate the concentration of the particles in the air.

2. The diluter as claimed in claim 1 further comprising a tubular porous grill mounted around an outer periphery of the filter.

3. The diluter as claimed in claim 1, wherein the inlet of the intake assembly is trumpet-like.

4. The diluter as claimed in claim 3, wherein the inlet has a small diameter that is smaller than a diameter of the second through hole.

5. The diluter as claimed in claim 4, wherein the first through hole has a diameter larger than a diameter of the second through hole.

6. The diluter as claimed in claim 1, wherein the inlet has a small diameter that is smaller than a diameter of the second through hole.

7. The diluter as claimed in claim 1, wherein the first through hole has a diameter larger than a diameter of the second through hole.

8. The diluter as claimed in claim 1, wherein the filter is made of a sheet filtering material and is folded to have multiple outer ridges and inner ridges, wherein plan faces are formed between every two adjacent outer ridge and inner ridge.

9. The diluter as claimed in claim 8, wherein the filter is made of a non-woven cloth.

10. A diluter comprising:
    at least two filtering assemblies each having
    a top cap that is provided with a first connector formed on a top face of the top cap and a first through hole defined through the top cap;
    a lower cap having a second connector securely formed on a bottom face of the lower cap, a second through hole defined through the lower cap and an assembly hole defined to communicate with the second through hole; and
    a tubular filter securely connected between the top cap and the lower cap to form a mixing zone in communication with the first and the second through holes; and
    an intake assembly having a first end and a second end, the first end being defined with a receiving hole to correspond to the first connector and the second end being provided with an inlet to communicate with the first end and the second end,
    whereby after the first connector of one of the at least two diluters is received in the receiving hole of the intake assembly and the assembly hole of one of the at least two diluters receives the first connector of the other one of the at least two diluters, the second connector of the other one of the at least two diluters is adapted to connect to a particle counter, the particle counter is able to calculate the concentration of the particles in the air.

11. The diluter as claimed in claim 10 further comprising a tubular porous grill mounted around an outer periphery of the filter.

12. The diluter as claimed in claim 10, wherein the inlet of the intake assembly is trumpet-like.

13. The diluter as claimed in claim 12, wherein the inlet has a small diameter that is smaller than a diameter of the second through hole.

14. The diluter as claimed in claim 13, wherein the first through hole has a diameter larger than a diameter of the second through hole.

15. The diluter as claimed in claim 10, wherein the inlet has a small diameter that is smaller than a diameter of the second through hole.

16. The diluter as claimed in claim 10, wherein the first through hole has a diameter larger than a diameter of the second through hole.

17. The diluter as claimed in claim 10, wherein the filter is made of a sheet of filtering material and is folded to have multiple outer ridges and inner ridges, wherein plan faces are formed between every two adjacent outer ridge and inner ridge.

18. The diluter as claimed in claim 10, wherein the filter is made of a non-woven cloth.

* * * * *